US011160454B2

United States Patent
Swaminathan et al.

(10) Patent No.: US 11,160,454 B2
(45) Date of Patent: Nov. 2, 2021

(54) SYSTEM AND METHOD FOR IMAGING BIOMARKERS INDICATIVE OF CARDIAC THERMAL ABLATION LESIONS

(71) Applicant: SUNNYBROOK RESEARCH INSTITUTE, Toronto (CA)

(72) Inventors: Venkat R. Swaminathan, Toronto (CA); Haydar Celik, Toronto (CA); Graham A. Wright, Toronto (CA)

(73) Assignee: Sunnybrook Research Institute, Ontario (CA)

(*) Notice: Subject to any disclaimer, the term of this patent is extended or adjusted under 35 U.S.C. 154(b) by 415 days.

(21) Appl. No.: 14/783,192

(22) PCT Filed: Apr. 8, 2014

(86) PCT No.: PCT/CA2014/050355
§ 371 (c)(1),
(2) Date: Oct. 8, 2015

(87) PCT Pub. No.: WO2014/165990
PCT Pub. Date: Oct. 16, 2014

(65) Prior Publication Data
US 2016/0058368 A1    Mar. 3, 2016

Related U.S. Application Data
(60) Provisional application No. 61/809,521, filed on Apr. 8, 2013.

(51) Int. Cl.
*A61B 5/00* (2006.01)
*A61B 5/055* (2006.01)
(Continued)

(52) U.S. Cl.
CPC .......... *A61B 5/0036* (2018.08); *A61B 5/0044* (2013.01); *A61B 5/0095* (2013.01);
(Continued)

(58) Field of Classification Search
CPC ... A61B 5/4836; A61B 5/0044; A61B 5/0095; A61B 5/055; A61B 5/0084; A61B 18/12;
(Continued)

(56) References Cited

U.S. PATENT DOCUMENTS 5,433,717 A * 7/1995 Rubinsky ............... A61B 18/02
600/411
6,575,969 B1 * 6/2003 Rittman, III ....... A61B 18/1482
128/898
(Continued)

FOREIGN PATENT DOCUMENTS

WO    20143/134786 A2    9/2013
WO    2014/082083 A1    5/2014

OTHER PUBLICATIONS

International Search Report dated Aug. 11, 2014 in connection with PCT/CA2014/050355.

*Primary Examiner* — Peter Luong
(74) *Attorney, Agent, or Firm* — Quarles & Brady LLP

(57) ABSTRACT

Described here are systems and methods for visualizing thermal ablation lesions by imaging specific chemical compounds that are created during thermal ablation procedures, such as cardiac ablation procedures. When a cardiac ablation procedure is performed, a central area of coagulative necrosis is created at the treatment site. This necrotic region is surrounded by layers of tissues with ultra-structural and electrophysiological changes. Two particular changes include the denaturation of proteins and the formation of ferric iron containing chemical compounds, such as methemoglobin and metmyoglobin. The formation of and distribution of such chemical compounds can be imaged with the appropriate systems and methods. Accordingly, these chemical compounds can be utilized as biomarkers that indicate the presence and physical characteristics of thermal ablation (Continued)

lesions. Imaging can be performed using magnetic resonance imaging, optical imaging, or photoacoustic imaging, as examples.

14 Claims, 2 Drawing Sheets

(51) Int. Cl.
*A61B 18/04* (2006.01)
*A61B 18/12* (2006.01)
*G01R 33/20* (2006.01)
*A61B 8/08* (2006.01)
*A61B 8/12* (2006.01)
*A61B 8/00* (2006.01)
*A61B 18/00* (2006.01)
*A61B 90/00* (2016.01)

(52) U.S. Cl.
CPC .............. *A61B 5/055* (2013.01); *A61B 18/04* (2013.01); *A61B 18/12* (2013.01); *A61B 5/0084* (2013.01); *A61B 8/0883* (2013.01); *A61B 8/0891* (2013.01); *A61B 8/12* (2013.01); *A61B 8/4416* (2013.01); *A61B 8/5246* (2013.01); *A61B 2018/00351* (2013.01); *A61B 2018/00577* (2013.01); *A61B 2018/00642* (2013.01); *A61B 2090/373* (2016.02); *A61B 2090/374* (2016.02); *A61B 2090/378* (2016.02); *G01R 33/20* (2013.01)

(58) Field of Classification Search
CPC .............. A61B 18/04; A61B 2090/378; A61B 2090/374; A61B 2090/373; A61B 2018/00642; A61B 2018/00577; A61B 2018/00351; A61B 8/0883; A61B 8/0891; A61B 8/12; A61B 8/4416; A61B 8/5246; G01R 33/20
See application file for complete search history.

(56) References Cited

U.S. PATENT DOCUMENTS

| | | | | |
|---|---|---|---|---|
| 7,220,254 | B2* | 5/2007 | Altshuler | A61B 18/203 128/898 |
| 2009/0093713 | A1* | 4/2009 | Hyde | A61B 34/30 600/427 |
| 2010/0110414 | A1 | 5/2010 | Colice | |
| 2010/0219829 | A1* | 9/2010 | Rehwald | G01R 33/4818 324/309 |
| 2013/0282001 | A1* | 10/2013 | Hezi-Yamit | A61B 18/18 606/33 |
| 2014/0114215 | A1* | 4/2014 | Melder | A61B 18/22 601/2 |

* cited by examiner

SYSTEM AND METHOD FOR IMAGING BIOMARKERS INDICATIVE OF CARDIAC THERMAL ABLATION LESIONS

CROSS-REFERENCE TO RELATED APPLICATIONS

This application represents the national stage entry of PCT International Application No. PCT/CA2014/050355 filed on Apr. 8, 2014, which claims the benefit of U.S. Provisional Patent Application Ser. No. 61/809,521, filed on Apr. 8, 2013, the disclosures of which are hereby incorporated by reference in their entirety for all purposes.

BACKGROUND OF THE INVENTION

The field of the invention is systems and methods for visualizing the effect of thermal ablation on cardiac tissue using a medical imaging system. More particularly, the invention relates to systems and methods for imaging specific biomarkers that indicate the effects of thermal ablation on cardiac tissue using a medical imaging system.

Catheter ablation therapies have become the first line of treatment for many cardiac arrhythmias. These procedures are traditionally performed under the guidance of x-ray fluoroscopy and involve guiding catheters to a region-of-interest in the subject's heart. Targeted energy is then used to ablate cardiac tissue in order to interrupt conduction in the region-of-interest, thereby mitigating the arrhythmia. Commonly, a 500 kHz radiofrequency ("RF") current is used as the energy source; however, other energy sources can be used in the alternative, including laser, ultrasound, microwave, and cryothermy. For some complex arrhythmias, such as atrial fibrillation, exclusive use of x-ray fluoroscopy guidance results in high recurrence rates, mainly due to the difficulty in visualizing soft-tissue cardiovascular organs. Other imaging modalities such as magnetic resonance imaging ("MRI"), computed tomography ("CT"), and intra-cardiac echocardiography have been investigated to improve outcomes.

The most common cause of high recurrence rates is inadequate energy delivery, which results in an insufficient lesion volume. Inadequate energy delivery can be caused by a lack of proper contact between the ablation electrode and the cardiac wall. Difficulties visualizing the soft tissues of the heart with x-ray imaging is one such source for the inadequate contact between the ablation electrode and cardiac wall. Inadequate contact can also happen due to edema, which reduces contact between the electrode and the heart wall. Other phenomena such as blood flow, which induces convective cooling, and the formation of coagulum around the electrode, which results in high impedance, also reduce the effective delivery of RF energy to tissue.

If follows that if ablation sites can be adequately monitored for effective lesion formation, recurrence rates and clinical outcomes can be significantly improved. Lesion assessment can happen either in real-time, in which the tissue is monitored while applying the RF energy, or just after ablation, in which the assessment is done after the procedure to verify the lesions. Lesion assessment can also be combined with a feedback loop to control the application of energy or to redo the ablation depending on the monitoring data.

In general, there are two types of lesion assessment: indirect assessment by monitoring the temperature of the electrode tip or the electrode-tissue contact, and direct assessment by imaging the ablated tissue itself. Common indirect assessment techniques include using robotic or magnetic catheter navigation systems, and performing temperature or force detection using sensors in the catheter tip. These indirect methods look at changes in tissue impedance, electrogram voltage, temperature of the tip, and contact force. By monitoring one or more of these parameters, good electrode tip contact with the tissue can be ensured. Indirect methods, however, are sensitive to multiple tissue changes beyond those directly reflecting thermal damage, including the frequent presence of edema and flow, which affect RF energy delivery even with good contact. Therefore, these indirect methods cannot be used to ensure adequate tissue ablation.

Direct assessment methods attempt to address these drawbacks. Common direct assessment methods include measuring tissue temperature using MR thermometry, which monitors tissue temperature using proton-resonant frequency ("PRF"), or temperature sensitive contrast agents. These direct methods, however, can only be performed during ablation and not after. Without a persistent indicator of damage, it is difficult to track the full extent of multiple lesions created over an extended period of time. Alternatively, tissue response, such as edema and flow disruption, can be imaged with methods, including those that characterize the dynamics and distribution of various contrast agents. These changes vary with time, even within the study period, and may not be sufficiently sensitive to identify the full extent of thermal damage. As such, these changes are not reliable indicators of adequate tissue ablation.

SUMMARY OF THE INVENTION

The present invention overcomes the aforementioned drawbacks by providing systems and methods for directly assessing cardiac thermal ablation procedures using specific properties of the ablated tissue to visualize and verify the ablation sites. The systems and methods work well even in the presence of edema and flow and have good contrast and signal-to-noise to be used in different modes for ablation treatment of cardiac arrhythmia.

It is an aspect of the invention to provide a method for imaging a biomarker indicative of thermal ablation using a medical imaging system. Data is acquired with the medical imaging system and from the data an image that depicts a biomarker indicative of a thermal ablation is produced.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
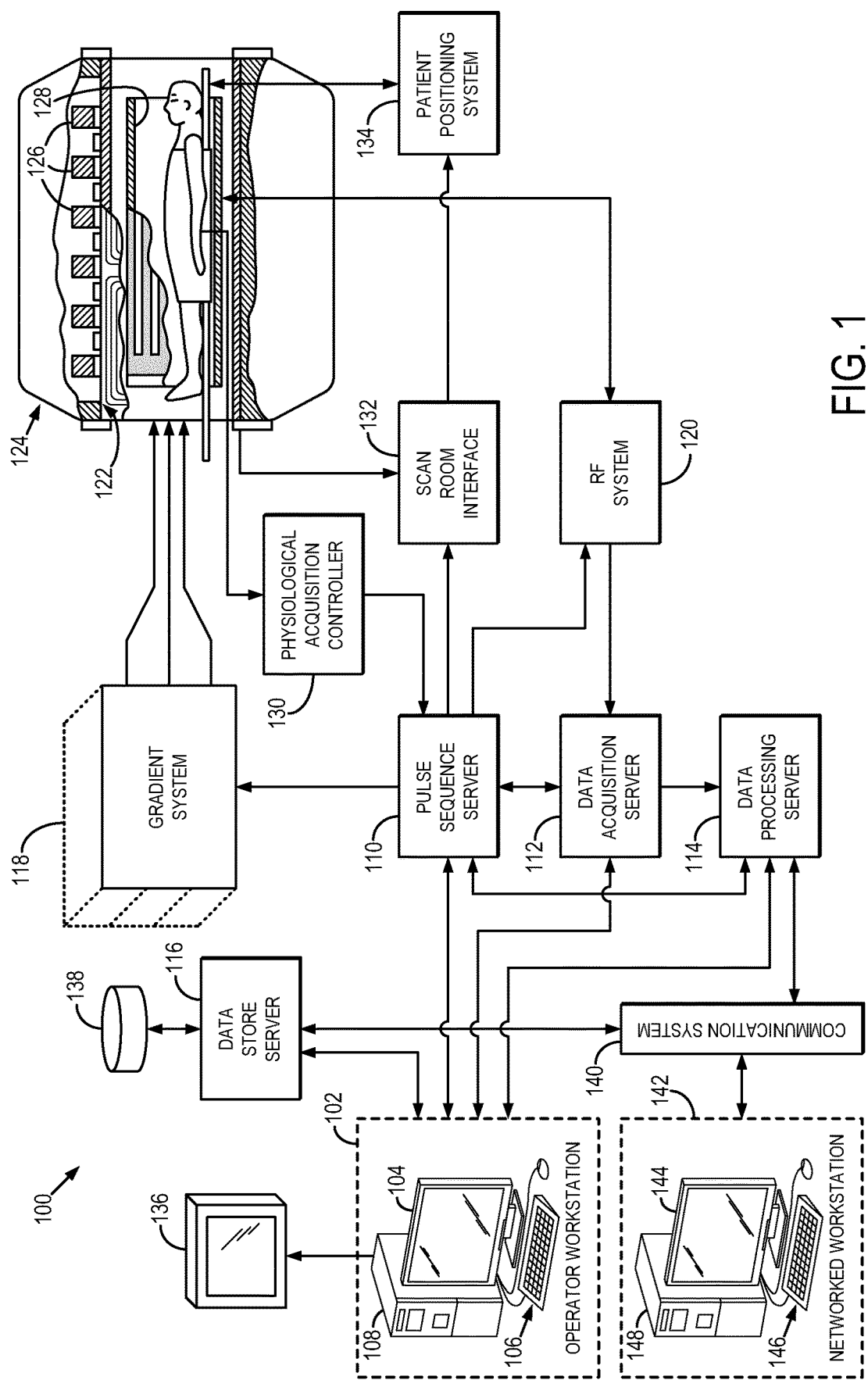
FIG. 1 is a block diagram of an example of a magnetic resonance imaging ("MRI") system that can implement some embodiments of the present invention.

Described here are systems and method for visualizing thermal ablation lesions by imaging specific chemical compounds that are created during thermal ablation procedures, such as cardiac ablation procedures. When a cardiac ablation procedure, or other thermal ablation procedure, is performed, a central area of coagulative necrosis is created at the treatment site. This necrotic region is surrounded by layers of tissues with ultra-structural and electrophysiological changes. Particular changes include the denaturation of proteins and the formation of chemical compounds containing ferric iron, such as methemoglobin and metmyoglobin. For instance, tissue proteins are denatured when they are heated above 140° F./60° C., and hemoglobin is converted to methemoglobin when blood is heated. The systems and methods of the present invention thus visualize the formation of and distribution of chemical compounds such as denatured proteins and chemical compounds containing ferric iron in ablated tissues. Accordingly, these chemical compounds can be referred to as thermal ablation markers that indicate the presence of thermal ablation lesions.

The thermal ablation markers can be detected based on measurable physical properties of the chemical compounds, including their magnetic resonance, optical absorbance, and optical reflectance properties. As one example, the presence of these chemical compounds can alter magnetic resonance signal parameters, including steady-state longitudinal magnetization, $M_0$; longitudinal relaxation time, $T_1$; and transverse relaxation time, $T_2$. As another example, optical absorbance or reflectance at specific wavelengths can be altered by the presence of these chemical compounds.

Some of these direct methods, such as methods based on $T_1$ relaxation, are modified from those developed for other organs, like liver and brain, whose physiology is very different from the heart. There is significant flow and motion in the heart and the development of edema in and around the area of ablation affects accurate visualization of the ablation site.

Multiple different imaging modalities can be used to visualize the markers, including magnetic resonance imaging ("MRI"), diffuse reflectance spectroscopy, Raman spectroscopy, and photoacoustic imaging. Using MRI, it is an advantage that both edema and the actual ablation area can be detected and differentiated. The optical and acoustic imaging modalities can be implemented for in vivo applications by using an appropriately designed intravascular catheter.

Turning first to MRI applications, the present invention allows for edema and cardiac thermal ablation lesions to be distinguished and visualized separately in vivo without the injection of a contrast agent. Prior imaging methods based on intrinsic contrast primarily used only $T_2$ weighting, which highlighted edema. Thus, cardiac edema was used as a marker for ablation, which is not strictly valid, as discussed above.

Methods that rely in the intrinsic contrast of $T_1$-weighting have largely not been investigated to date. When a $T_1$-weighted imaging method has been used to assess thermal ablation procedures, it was found that it closely matched $T_2$-weighted imaging, as described by T. Dickfield, et al., in "Characterization of acute and subacute radiofrequency ablation lesions with nonenhanced magnetic resonance imaging," *Heart Rhythm,* 2007; 4:208-214. It is a discovery of the present invention that $T_1$ weighting provides significantly different information than $T_2$ weighting as they relate to visualizing thermal ablations. For instance, it is a discovery of the present invention that while $T_2$ weighting appropriately depicts edema, $T_1$ weighting visualizes the actual ablation lesion. These differences provide a choice of imaging sequences to depict different characteristics thermal ablation sites. Using the systems and methods described here, thermal ablation lesions can be visualized as early as a few minutes after an ablation treatment.

Proteins in cardiac tissue are denatured when heated and thus have a shortened longitudinal relaxation time, $T_1$, relative to proteins that are not denatured. Chemical compounds containing ferric iron, such as methemoglobin or metmyoglobin, which are generated when cardiac tissue is heated during a thermal ablation procedure, effectively act as intrinsic paramagnetic contrast agents by shortening the $T_1$ relaxation time of nearby tissues. It follows that a $T_1$-weighted imaging method can be used to produce an image that depicts a contrast influenced by and indicating the presence of denatured proteins and chemical compounds containing ferric iron produced during a cardiac thermal ablation procedure. Such an imaging method can thus provide a visualization of the actual area of lesion generated during the cardiac thermal ablation procedure. Methods with inversion recovery or saturation preparation can be used to enhance the $T_1$-weighting of the desired images of the subject. These magnetization preparation modules can be combined with either a gradient-echo ("GRE") pulse sequences, with or without spoiling; or a steady-state free precession ("SSFP") pulse sequence.

Both GRE and SSFP can be performed in a segmented manner to achieve good signal-to-noise ratio ("SNR") within a single breath hold. To monitor lesion formation in real-time during a cardiac thermal ablation procedure, however, a snapshot inversion-prepared SSFP technique is particularly effective because it can produce a $T_1$-weighted image in a single heartbeat.

The above techniques can be extended as three dimensional acquisitions for volume coverage of the ablation extent. These are particularly helpful for verifying the lesion area and identifying gaps in lesions after the ablation procedure with a high isotropic spatial resolution. When the acquisition time becomes too high to fit in a single breath hold, they can be used with respiratory-motion compensation techniques like navigators. To reduce the time of acquisition, these can also be combined with undersampled reconstruction techniques like parallel imaging or compressed sensing.

When the ablation procedure is repeated after a few weeks or months, perhaps due to recurrence of arrhythmia, there is a clinical need to differentiate between newly-created acute lesions and chronic lesions. The above-mentioned imaging techniques can be implemented to this end. For instance, over days to weeks, ferric iron and/or denatured proteins produced in response to a thermal ablation procedure will be removed by macrophages. As a result of these chemical compounds being removed from the treated sites, the presence of these chemical compounds will be diminished in chronic lesions. Methods that image the distribution of paramagnetic contrast agents, such as gadolinium-based contrast agents, can be used to produce images with contrast that is sensitive to the fibrosis seen in chronic thermal ablation lesions. A $T_1$-mapping technique can also be used to provide this information. For example, the following $T_1$ mapping techniques for the heart can be used to this end: MOLLI, described by D. R. Messroghli, et al., in, "Modified Look-Locker inversion recovery (MOLLI) for high-resolutionT1 mapping of the heart," *Magnetic Resonance in Medicine,* 2004; 52:141-146; shMOLLI, described by S. K. Piechnik, et al., in "Shortened Modified Look-Locker Inversion recovery (ShMOLLI) for clinical myocardial T1-mapping at 1.5 and 3 T within a 9 heartbeat breathhold," *Journal of Cardiovascular Magnetic Resonance,* 2010; 12, 69; and MLLSR, described by T. Song, et al., in "Flexible cardiac T1 mapping using a modified look-locker acquisition with saturation recovery," *Magnetic Resonance in Medicine,* 2012; 67:622-627.

In addition to delineating the actual ablation area, it is desirable to be able to visualize edema because edema frequently interferes with effective RF ablation delivery. In these situations, $T_2$-weighted or $T_2$ mapping techniques can be used. $T_2$-weighted techniques, such as a black-blood triple inversion-recovery sequence, highlight regions of edema due to their enhanced $T_2$ weighting. A $T_2$ mapping technique, in addition, can be used to quantify edema and to characterize edema progression over time.

If $T_1$-weighted ablation visualization methods and $T_2$-weighted edema mapping methods are employed separately in different breath holds, there is a chance of misregistration between them due to different breath holding positions. A simultaneous $T_1$ and $T_2$ weighted (or mapping) sequence in the same breath hold wouldn't have this effect. An example of such a sequence is inversion-prepared CINE SSFP imaging, where a CINE sequence is modified with the application of an inversion pulse every few heartbeats, such as the one described by J. S. Detsky, et al., in "Inversion-recovery-prepared SSFP for cardiac-phase-resolved delayed-enhancement MRI," *Magnetic Resonance in Medicine,* 2007; 58:365-372. The signal evolution in the IR-SSFP CINE sequence is characterized by the $T_1^*$ relaxation time, which is dependent on both $T_1$ and $T_2$. Different temporal phases of this sequence have different $T_1/T_2$ weightings. Another example is the $T_2$ mapping sequence itself, where the fitted $M_0$ and $T_2$ terms can be used for $T_1$-weighting and $T_2$-weighting, respectively.

It should be noted that all of the above techniques do not require the administration of gadolinium-based MRI contrast agents, though they do work after the administration of contrast. After a contrast dose, the $T_1$ values will primarily be dependent on the local contrast agent distribution of the tissues.

$T_2$ mapping can be performed using a multi-echo fast-spin-echo ("MEFSE") sequence and $T_1^*$ characterization using a 2RR-IR-SSFP CINE method. As an example, both MEFSE and IRSSFP can be performed soon after the creation of thermal ablation lesions.

MEFSE images were fitted using a standard 2-parameter fit for $M_0$ and $T_2$, $$S = M_0 e^{-\frac{TE}{T_2}}. \qquad (1)$$

The $M_0$ term here is a function of both true equilibrium $M_0$ and $T_1$ because it was a single-RR (RR=700 ms) sequence. IR-SSFP signal recovery is determined by $T_1^*$, which as noted above is dependent on both $T_1$ and $T_2$. The $T_2$ and $M_0$ maps and IR-SSFP images can be analyzed using an ROI based analysis to compare the signal in three zones: an ablation lesion zone, an adjacent edema zone, and a remote tissue zone.

On $T_2$ maps, there is a broad area of increased $T_2$ in and around the ablation, likely due to edema, that is much larger than the actual extent of the lesion. However the $M_0$ maps correspond closely with the actual border of ablation. Contrast in $T_1^*$-weighted IR-SSFP images also clearly depicts the actual border of the ablation, with the ablation zone reflecting a significantly shorter $T_1^*$. Two phases in the IR-SSFP images, one that visualizes edema and one that visualizes actual ablation lesion, can be selected. Phases soon after the inversion pulse (inversion time 100 to 150 ms) visualize edema and later phases which have dark blood (inversion time 600 to 800 ms) visualize the ablation lesion.

The $M_0$ and $T_2$ maps appear to depict actual lesion area and edema respectively. $T_1^*$-weighted IR-SSFP generally gives more robust visualization of the ablation lesion within a breath-hold. It is contemplated that the high signal of the lesion core in $T_1$-weighted and $T_1^*$-weighted images is due to denaturation of proteins and formation of chemical compounds containing ferric iron, such as methemoglobin and metmyoglobin, which are created upon heating blood. In summary, $T_1$-weighting seems to delineate the acute lesion core while $T_2$-weighting seems to depict the overlying edema. Combinations of these images can thus be used to differentially visualize edema and lesions caused by thermal ablation.

Referring particularly now to FIG. 1, an example of a magnetic resonance imaging ("MRI") system 100 is illustrated. The MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Because the $T_1$-weighted imaging signal change is primarily caused by the creation of denatured proteins and chemical compounds containing ferric iron, including methemoglobin and metmyoglobin, during ablation, other imaging modalities based on the optical or acoustic properties of these chemical compounds can be used to detect thermal ablations as well. As an example, optical properties of methemoglobin or metmyoglobin can be exploited by incorporating optical detection techniques into catheters for intracardiac use.

The heme group of methemoglobin and metmyoglobin contains ferric iron ($Fe^{3+}$), instead of ferrous iron ($Fe^{2+}$), which is found in oxyhemoglobin, deoxyhemoglobin, and myoglobin. This makes methemoglobin and metmyoglobin detectable using optical or acoustic techniques.

Methemoglobin formed in skin ablation lesions created by a pulsed dye laser has been detected using diffuse reflectance spectroscopy ("DRS") in the visible to near-infrared spectrum. A similar setup with a hand-held fiber-optic surface probe connected to a spectrometer was used in measuring myocardial tissue oxygenation during coronary artery bypass graft surgery. Another related technique, broadband diffuse optical spectroscopy has been used to monitor in-vivo methemoglobin formation in the blood non-invasively. Using similar equipment suitably modified for cardiac catheterization, methemoglobin and metmyoglobin created during cardiac ablations can be detected using visible to near-infrared spectroscopy.

Raman spectroscopy has also been found to detect methemoglobin. More recently, it has been found to detect methemoglobin in whole blood or even in a single red blood cell. Fiber-optic probes have been developed for Raman spectroscopy for use in gastro-intestinal applications like endoscopy. A similar probe for cardiac catheterization applications can detect methemoglobin and metmyoglobin created during cardiac electrophysiology ablation procedures.

Figure 2:
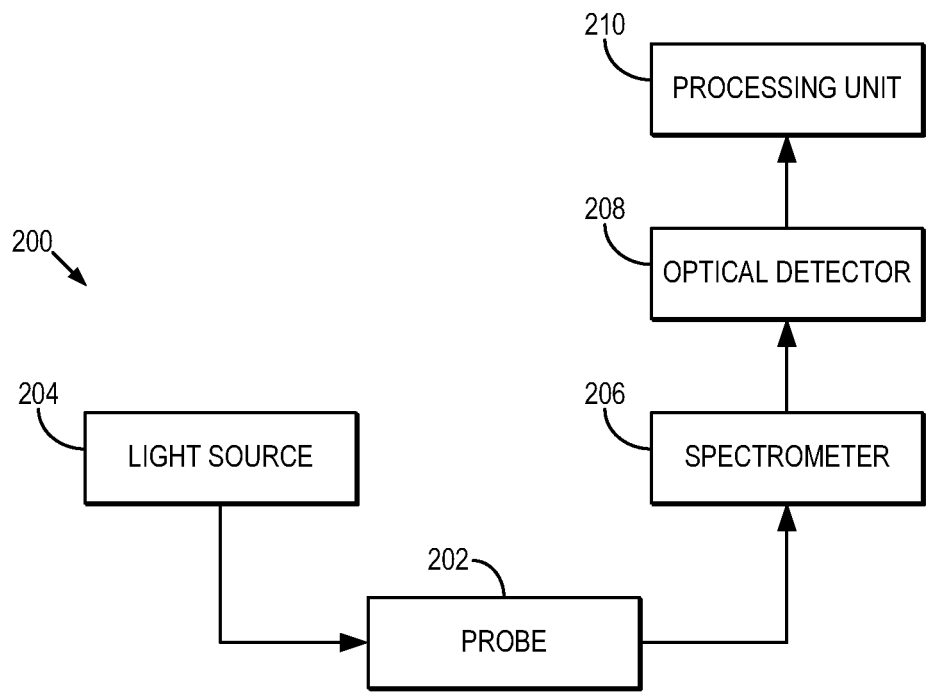
FIG. 2 is a block diagram of an example of an optical spectrometer system that can be configured to perform diffuse reflectance spectroscopy or Raman spectroscopy, and that can implement some embodiments of the present invention.

Referring now to FIG. 2, an example of an optical spectrometer system 200 that includes a fiber optic probe 202 is illustrated. In some embodiments, the fiber optic probe 202 can be incorporated into an intravascular or endoscopic device, such as an intravascular catheter or an endoscope. The optical spectrometer system also includes a light source 204, a spectrometer 206, an optical detector 208, and a processing unit 210. In some embodiments, the optical spectrometer system 200 may also include a monochromator that is optically coupled to the light source 204. As an example, the monochromator may include a scanning double-excitation monochromator.

The optical spectrometer system 200 can be configured to perform any number of different optical spectroscopy techniques, including diffuse reflectance spectroscopy ("DRS"), diffuse optical spectroscopy, and Raman spectroscopy.

Light, or other electromagnetic radiation, is provided by the light source 204 and communicated via an optical fiber to the fiber optic probe 202, where the light or other electromagnetic radiation is transmitted into a sample, object, or subject. As one example, the light source 204 may include a white light source, and as another example, may include a laser. Light, or other electromagnetic radiation, is received by the fiber optic probe 202 and communicated to the spectrometer 206 via an optical fiber. The fiber optic probe 202 may include at least one emitting fiber for emitting the light, or other electromagnetic radiation, into the sample, object or subject. The fiber optic probe 202 may also include at least one collecting fiber for collecting light, or other electromagnetic radiation, that has interacted with the sample, object, or subject.

The optical detector 208 is optically coupled to the spectrometer 206 and acquires data based on the light, or other electromagnetic radiation, entering the spectrometer 206 from the fiber optic probe 202. In some embodiments, the optical detector 208 may include a charged-couple device ("CCD") unit. The data acquired by the optical detector 208 is communicated to the processing unit 210 for processing, such as the generation of spectra and images of the sample, object, or subject.

As an example, the processing unit 210 includes a commercially available computer system, including a processor, a memory or other data storage device, a display, and input devices, such as a keyboard and mouse. The processing unit 210 can be configured to convert the collected electromagnetic radiation to at least one of absorption and scattering data, from which reflectance spectra can be produced. The processing unit 210 can also be configured to convert the collected electromagnetic radiation to data from which Raman spectra can be produced.

Photoacoustic imaging is a method that delivers laser pulses to biological tissues and detects the resulting ultrasonic waves. It has recently been used to detect methemoglobin in skin lesions, and has been integrated into catheters for combined photoacoustic and intravascular ultrasound ("IVUS") imaging. Repurposing the catheters for cardiac imaging, cardiac ablation lesion creation can be detected using methemoglobin or metmyoglobin as markers.

Figure 3:
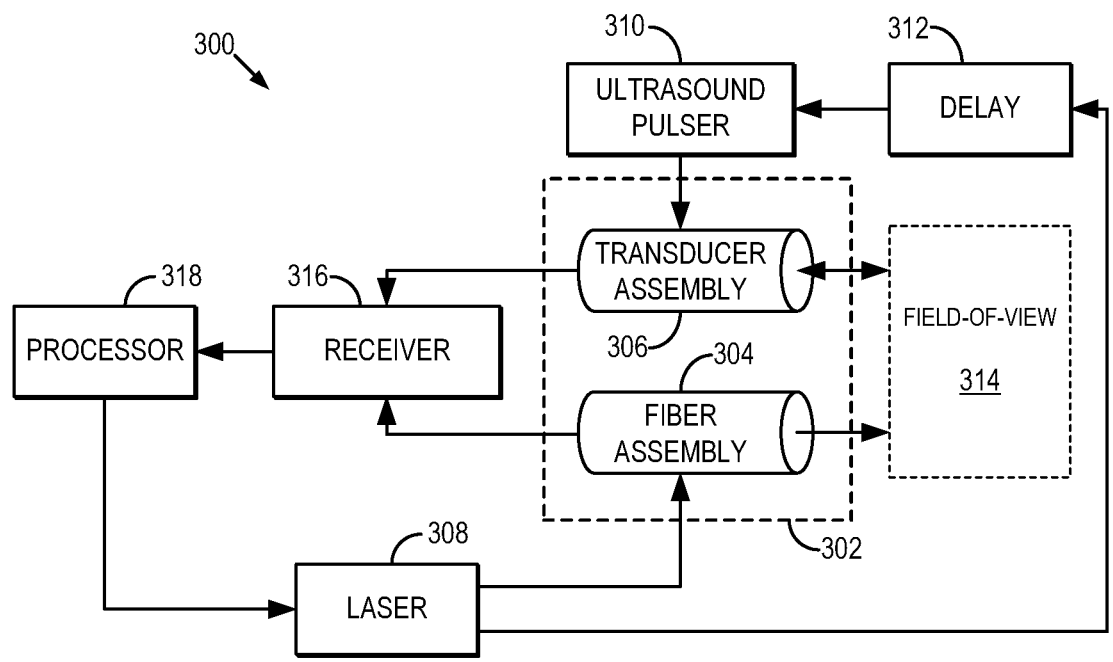
FIG. 3 is a block diagram of an example of a photoacoustic imaging system that can implement some embodiments of the present invention.

Referring now to FIG. 3, a block diagram of an example photoacoustic imaging system 300 that incorporates an photoacoustic imaging device 302 is illustrated. The photoacoustic imaging device 302 generally includes a fiber assembly 304 and a transducer assembly 306, which may be coupled together. For instance, the fiber assembly 304 and transducer assembly 306 may be coupled via a common outer sheath that holds the fiber assembly 304 and transducer assembly 306 in spaced arrangement.

The fiber assembly 304 includes at least one optical fiber. A light source 308 is optically coupled to the fiber assembly 304 and delivers light to the distal end of the fiber assembly 304 to irradiate the object being imaged. In some embodiments, the light source 308 is a laser source, which may be a continuous wave laser source or a pulse wave laser source. In some embodiments, the light source 308 may include multiple laser systems or diodes, thereby providing different optical wavelengths, that are fed into one or more optical fibers. The selection of an appropriate excitation wavelength for the light source 308 is based on the absorption characteristics of the imaging target. Because the average optical penetration depth for intravascular tissue is on the order of several to tens of millimeters, the 400-2100 nm wavelength spectral range is suitable for intravascular photoacoustic applications. Thus, in some embodiments, the light source 308 may be an Nd:YAG (neodymium-doped yttrium aluminum garnet) laser that operates at 1064 nm wavelength in a continuous mode.

The transducer assembly 306 generally includes an photoacoustic transducer for receiving photoacoustic signals generated by an illumination field, such as an illumination field generated by pulsed or continuous wave laser light. In some configurations, the photoacoustic transducer can also be operated to generate ultrasound energy and to receive pulse-echo ultrasound emissions. In this configuration, the photoacoustic transducer can be operated in a receive-only mode for photoacoustic imaging and, when the illumination field is not being generated, the photoacoustic transducer can also be operated in an ultrasound imaging mode to obtain ultrasound images. In some configurations, the photoacoustic transducer may include multiple transducer elements, some of which may be dedicated solely for receiving photoacoustic signals while others may be dedicated solely to generating and receiving pulse-echo ultrasound signals.

In some other configurations, the transducer assembly 306 may include at least two transducers: a dedicated photoacoustic transducer and a dedicated ultrasound transducer for generating and receiving pulse-echo ultrasound signals. In this dual-transducer configuration, both photoacoustic and ultrasound images can be obtained. With the dual-transducer configuration, photoacoustic and ultrasound images can be obtained simultaneously and, even when not obtained simultaneously, are innately co-registered given the spatial relationship between the photoacoustic transducer and the ultrasound transducer.

Irradiation with the light source 308 is performed at a given point for a finite amount of time with an optical excitation waveform. In frequency-domain photoacoustic applications, in which a continuous wave laser is used, the optical excitation waveform may be amplitude modulated with frequency sweeping, such as a chirp or pulse train. The irradiation produced by this type of optical excitation results in a frequency-domain photoacoustic modulated signal being produced in the region illuminated by the photoacoustic imaging device 302. The chirp can include a multitude of different excitation waveforms including linear, non-linear, and Gaussian tampered frequency swept chirps.

When used to obtain ultrasound images, operation of the transducer assembly 306 may be controlled by an ultrasound pulser 310, which provides ultrasound excitation waveforms to the transducer assembly 306. In single-transducer configurations in which the photoacoustic transducer is used to both receive photoacoustic signals and to generate and receive pulse-echo ultrasound signals, a delay 312 between the light source 308 and the ultrasound pulser 310 provides a trigger signal that directs the ultrasound pulser 310 to operate the photoacoustic transducer at a delay with respect to the irradiation of the field-of-view 314. The timing provided by the delay 312 enables the detection of photoacoustic signals by the photoacoustic transducer in the transducer assembly 306 when the field-of-view 314 is being illuminated, but also the generation and detection of pulse-echo ultrasound signals when the field-of-view 314 is not being illuminated.

Signals received by the transducer assembly 306 are communicated to a receiver 316, which generally includes a pre-amplifier, but may also include one or more filters, such as bandpass filters for signal conditioning. The received signals are then communicated to a processor 318 for analysis.

Thus, the generated photoacoustic signals are detected by the photoacoustic transducer in the transducer assembly 306, communicated to the receiver 316, and then communicated to the processor 318 for processing and/or image generation. As one example, the photoacoustic signals can be processed in accordance with the methods described above to monitor the physical changes in a tissue following the administration of a treatment, such as a radiation treatment or a chemotherapy treatment. Similarly, pulse-echo ultrasound signals received by either the photoacoustic transducer or a dedicated ultrasound transducer in the transducer assembly 306 can also be communicated to the receiver 316 and then communicated to the processor 318 for processing and/or image generation.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for imaging a biomarker indicative of thermal ablation using a magnetic resonance imaging (MRI) system, the steps of the method comprising:
   a) acquiring data with the MRI system at least one of during a thermal ablation procedure and after a thermal ablation procedure;
   b) producing from the acquired data, an image having pixel values depicting a magnetic resonance signal parameter that is affected by the thermal ablation procedure; and
   c) determining the biomarker by monitoring the formation and distribution of a ferric iron containing chemical compound in the image, wherein the biomarker comprises the magnetic resonance signal parameter as affected by the presence of the ferric iron containing chemical compound produced in response to the thermal ablation procedure.

2. The method as recited in claim 1 in which the ferric iron containing chemical compound is selected from the group consisting of methemoglobin, metmyoglobin, and combinations thereof.

3. The method as recited in claim 1 in which the magnetic resonance signal parameter is at least one of a longitudinal magnetization, $M_0$; a longitudinal relaxation time, $T_1$; a transverse relaxation time, $T_2$; and a relaxation time that accounts for both longitudinal and transverse relaxation, $T_1^*$.

4. The method as recited in claim 3 in which step b) includes producing a $T_2$ map having pixel values indicative of $T_2$ values.

5. The method as recited in claim 3 in which step b) includes producing a $T_1^*$ map having pixel values indicative of $T_1^*$ values.

6. The method as recited in claim 3 in which step b) includes producing a $T_1$ map having pixel values indicative of $T_1$ values.

7. The method as recited in claim 6 further comprising identifying a thermal ablation lesion in the $T_1$ map and quantifying an age of the identified thermal ablation lesion based on $T_1$ values at pixels locations associated with the identified thermal lesion.

8. The method as recited in claim 1 further comprising monitoring lesion formation in real-time during a cardiac thermal ablation procedure by repeatedly performing steps a) and b) using an inversion-recovery steady-state free precession pulse sequence in step a) to acquire data in a single heartbeat.

9. The method as recited in claim 1, wherein the ferric iron containing chemical compound consists of methemoglobin.

10. The method as recited in claim 1, wherein the ferric iron containing chemical compound consists of metmyoglobin.

11. The method as recited in claim 1, wherein the ferric iron containing chemical compound comprises both methemoglobin and metmyoglobin.

12. The method as recited in claim 1, wherein the data acquired with the MRI system are $T_1^*$-weighted data indicative of tissues having shortened longitudinal relaxation times caused by ferric iron containing chemical compounds nearby the tissues.

13. The method as recited in claim 1, further comprising acquiring second data with the MRI system and producing from the second data a second image that depicts edema, such that the image and the second image differentiate thermal ablation area and edema, respectively.

14. The method as recited in claim 13, wherein the data acquired with the MRI system are one of $T_1$-weighted data or $T_1^*$-weighted data, and the second data acquired with the MRI system are $T_2$-weighted data.

* * * * *